US00PP24359P3

(12) United States Plant Patent
Arkinstall

(10) Patent No.: US PP24,359 P3
(45) Date of Patent: Apr. 1, 2014

(54) **SHRUB TYPE PLANT *ROSA* PLANT NAMED 'NOASPLASH'**

(50) Latin Name: ***Rosa* hybrid**
Varietal Denomination: Noasplash

(75) Inventor: Sean Arkinstall, Gisborne (AU)

(73) Assignee: Reinhard Noack (DE)

( * ) Notice: Subject to any disclaimer, the term of this patent is extended or adjusted under 35 U.S.C. 154(b) by 88 days.

(21) Appl. No.: 13/385,095

(22) Filed: Jan. 31, 2012

(65) Prior Publication Data

US 2013/0198915 P1 Aug. 1, 2013

(51) Int. Cl.
*A01H 5/00* (2006.01)

(52) U.S. Cl.
USPC ..... Plt./102; Plt./101

(58) Field of Classification Search
USPC ..... Plt./101–151
See application file for complete search history.

*Primary Examiner* — Susan McCormick Ewoldt
(74) *Attorney, Agent, or Firm* — Cassandra Bright

(57) ABSTRACT

A new and distinct shrub type *Rosa* hybrid named 'Noasplash' is disclosed, characterized by excellent resistance to common diseases of *Rosa* in the landscape, including blackspot, mildew and rust. Plants produce unique bi color bright pink/light pink flowers. Plant form is compact, with arching branches forming a spreading plant, especially suited for landscape applications. The new cultivar is a *Rosa* typically suited for ornamental container and landscape use.

2 Drawing Sheets

Latin name of the genus and species: *Rosa* hybrid.
Variety denomination: 'Noasplash'.

BACKGROUND OF THE INVENTION

The new cultivar is the result of a chance discovery in a commercial nursery in Gisborne, Victoria, Australia. The inventor, Sean Arkinstall, a citizen, of Australia, discovered the new variety as a single whole plant mutation of the parent variety, *Rosa* hybrid 'Flower Carpet Appleblossom', U.S. Plant Pat. No. 10,239. The discovery was made February 2006.

After selecting the new cultivar, asexual reproduction of 'Noasplash' was first performed by vegetative cuttings at a commercial nursery in Victoria, Australia in 2006. 'Noasplash' has since produced six generations and has shown that the unique features of this cultivar are stable and reproduced true to type.

SUMMARY OF THE INVENTION

The cultivar 'Noasplash' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Noasplash'. These characteristics in combination distinguish 'Noasplash' as a new and distinct *Rosa* hybrid cultivar:

1. Excellent resistance to common diseases of *Rosa* in the landscape, including blackspot, mildew and rust.
2. Compact, spreading plant habit, especially suited for landscape applications.
3. Arching branches.
4. Unique bi color bright pink/light pink flower color
5. Shrub type rose plant. .

PARENTAL COMPARISON

Plants of the new cultivar 'Noasplash' are similar to the parent, *Rosa* hybrid 'Flower Carpet Appleblossom' U.S. Plant Pat. No. 10,239 in most horticultural characteristics. However, 'Noasplash' differs in flower color. Flowers of the parent variety are light pink, whereas plants of the new variety produce bi color bright pink/light pink flowers.

COMMERCIAL COMPARISON

Plants of the new cultivar 'Noasplash' can be compared to the unpatented commercial variety *Rosa* hybrid 'Delstrjor'. 'Noasplash' differs from 'Delstrjor' in flower size. 'Noasplash' has a medium sized flower, whereas 'Delstrjor' has a large sized flower.

BRIEF DESCRIPTION OF THE PHOTOGRAPHS

Figure 1:
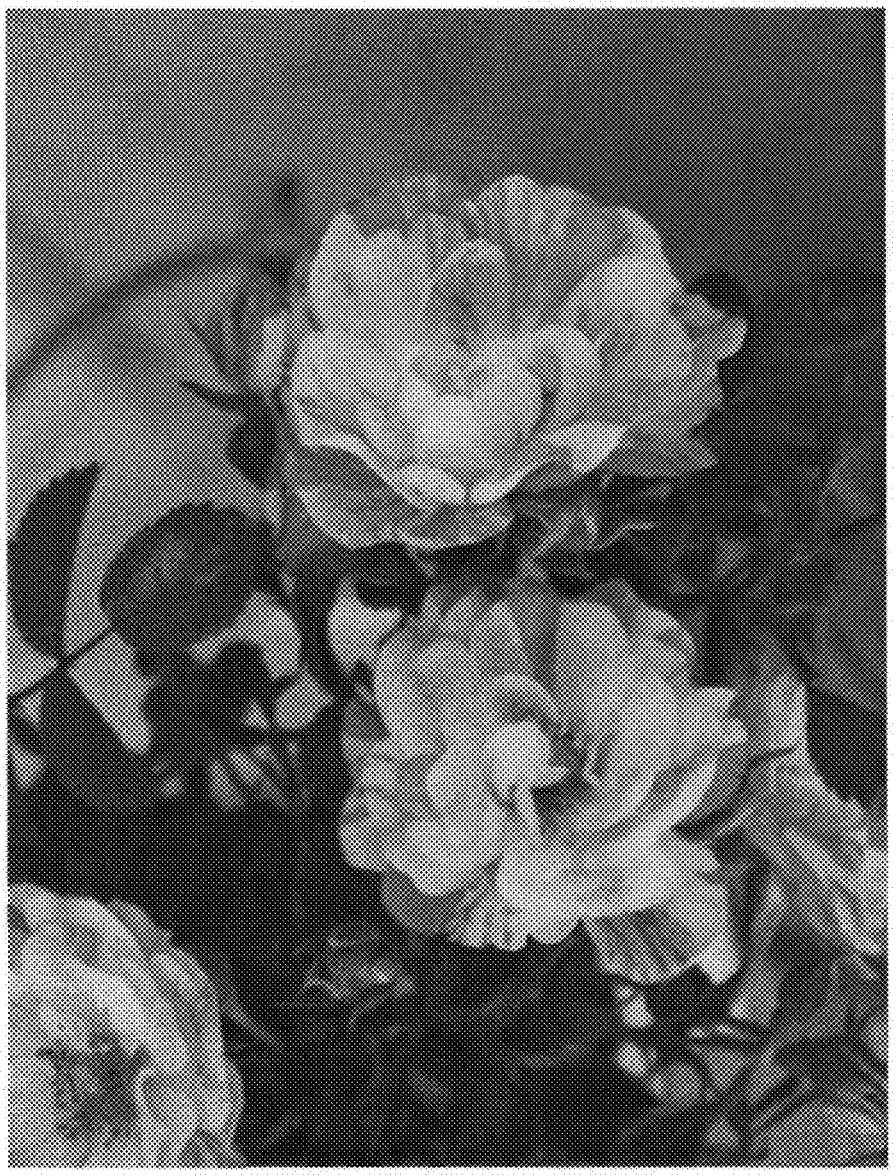

The accompanying photograph in FIG. 1 illustrates in full color a typical flower of 'Noasplash' grown outdoors in Silvan, Victoria Australia.

Figure 2:
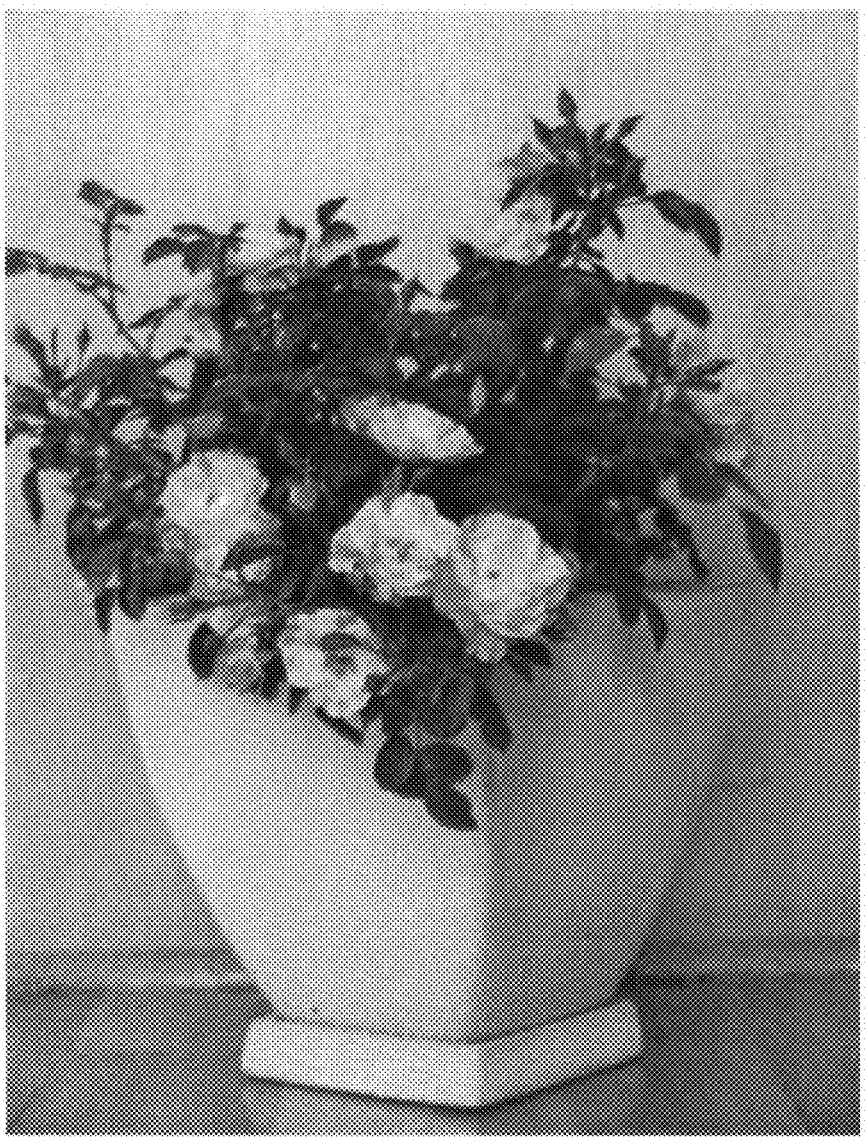

FIG. 2 illustrates in full color a typical plant of 'Noasplash' grown outdoors in Silvan, Australia. The plant is approximately 12 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Noasplash' plants grown outdoors in Melbourne, Australia, described during mid summer. Plants were grown in the ground, given a hard winter pruning, typical of garden rose cultivation. The growing temperature ranged from −1° C. to 18° C. at night to 4° C. to 40° C. during the day. No artificial light, photoperiodic treatments or chemical treatments were given to the plants. Measurements and numerical values represent averages of typical flowering types.

Botanical classification: *Rosa* hybrid 'Noasplash'.

Commercial classification: Shrub.

Age of the plant described: Approximately 2 years.

Container size of the plant described: In ground.

PROPAGATION

Typical method: Vegetative cuttings.

Time to rooting: Approximately 20 days at 20° C.

Time to produce a rooted plantlet: Approximately 55 days at 15° C.

Root description: Fibrous.

PLANT

Growth habit: Low and spreading with and arching habit to the branches.

Height: Approximately 60 to 80 cm.

Plant spread: Approximately 100 cm.

Rootstock: Self, ungrafted or budded.

Growth rate: Approximately 6 months to reach 60 to 80 cm.

Branching characteristics: Numerous lateral branches in an arching habit.

Length of primary lateral branches: Approximately 60 to 80 cm.

Diameter of lateral branches: Approximately 1 cm.

Quantity of lateral branches: Numerous.

Branching arrangement: Emerging from base of plant.

Branches-young wood:

- *Diameter*.—Approximately 0.5 to 1.0 cm.
- *Texture*.—Smooth.
- *Approximately density/quantity of thorns*.—Irregularly spaced, moderate/average amount for a landscape rose.
- *Color*.—Near RHS Green 143B.

Branches-old wood:

- *Diameter*.—Approximately 1.5 cm, after 2 years.
- *Texture*.—Smooth.
- *Approximately density/quantity of thorns*.—Moderate density, irregularly spaced.
- *Color*.—Near RHS Green143D, with brown tinge, not RHS identified.

FOLIAGE

Leaf:

- *Arrangement*.—Alternate, pinnate.
- *Quantity*.—Approximately 20 per main branch, with 7 leaflets per leaf.
- *Average length*.—Approximately 14 cm.
- *Average width*.—Approximately 8 cm.
- *Leaflets*.—Average Length: Approximately 3.5 cm. Average Width: Approximately 2.5 cm. Shape of blade: Ovate. Apex: Acute. Base: Attenuate. Margin: Serrate. Texture of top surface: Glabrous, leathery. Texture of bottom surface: Rugose. Pubescence: non-pubescent. Leaf internode length: Average 2.0 to 5.0 cm. Color: Young foliage upper side: Near RHS Green 143A. Young foliage under side: Near RHS Yellow-Green 144A. Mature foliage upper side: Near RHS Green 134B. Mature foliage under side: Near RHS Green 135D.
- *Venation*.—Type: Pinnate. Venation color upper side: Near RHS Green 143A, and Green 134B, both colors present. Venation color under side: Near Yellow-Green 144A to Green 135D. Reddish tinge, unidentified by RHS color chart.
- *Petiole*.—Length: 4 cm. Width: 1.2 to 1.5 cm at base. Color: Near RHS Green 143A. Texture: Glabrous.

FLOWER

Natural flowering season: Continuous flowering from late Spring to mid Fall.

Begins flowering after how many years/months: 3 months from a rooted cuttings.

Inflorescence type and habit: Spray, arrangement of somewhat flattened, single flowers.

Rate of flower opening: Approximately 7 days from bud to fully opened flower.

Flower longevity on plant: 5 days, after fully opened.

Quantity of flowers: Approximately 30 to 45 flowers an developing buds per stem, with approximately 100 to 250 flowers and developing buds per plant.

Inflorescence size:

- *Diameter*.—Approximately 5 cm.
- *Depth*.—Approximately 2 cm.

Peduncle:

- *Length*.—Approximately 1.5 to 2.0 cm.
- *Diameter*.—Approximately 1.0 to 1.5 mm.

Petals:

- *Petal arrangement*.—Overlapping whorl.
- *Size*.—Variable, an average of typical small petals: Length: Approximately 2.5 cm. Width: Approximately 2.0 cm.
- *Shape*.—Ellitical.
- *Margin*.—Entire, upwardly curved.
- *Apex*.—Emarginate.
- *Base*.—Rounded.
- *Petal quantity*.—Average 15 to 20.
- *Texture*.—Smooth.

Color:

- *Petals*.—When opening: Upper surface: Bi colored petals near RHS Red-Purple 65C and 67C. Lower surface: Bi color petals vary from Red-Purple 69C and 67C. Fully opened: Upper surface: Bi colored petals near RHS Red-Purple 65C and 67C. Lower surface: Bi color petals vary from Red-Purple 69C and 67C. Color Changes when aging: Fades significantly in hot weather.

Bud:

- *Shape*.—Spherical.
- *Length*.—Approximately 2.5 cm.
- *Diameter*.—Approximately 1.5 cm.
- *Color*.—Varies from Red-Purple 69C and 67C.
- *Sepals*.—Length: Approximately 1.5 cm. Width: Approximately 0.5 cm. Shape: Lanceolate. Color Interior Surface: RHS Green 143C. Exterior Surface: RHS Green 143A with reddish tinge not measurable by RHS color chart. Texture: Densely puberulent.
- *Receptacle*.—Length: 0.06 to 1.0 cm. Width: 0.6 to 0.08 cm. Shape: pitcher shaped. Color: Near RHS Green 143A when immature, maturing to Red-Purple 59A.
- *Fragrance*.—None.

REPRODUCTIVE ORGANS

Stamens:

*Number*.—Numerous.

*Filament length*.—Approximately 0.5 cm.

*Filament color*.—Cream to light yellow, RHS color indeterminable.

Anthers:

*Length*.—1 mm.

*Shape*.—Narrow ovate.

*Color*.—Near RHS Greyed-Orange 166A.

*Pollen*.—Color: Near RHS Yellow 15A. Quantity: Abundant.

Pistil:

*Number*.—Numerous.

*Length*.—Approximately 4 mm.

*Color*.—Near RHS Greyed-Yellow 160C.

*Style*.—Length: Approximately 2.0 cm. Color: Light green to cream, RHS color indeterminable.

*Stigma*.—Color: Cream to light yellow, RHS color indeterminable.

OTHER CHARACTERISTICS

Seeds and fruits: Hips small, round, cupped. Green with reddish tint.

Disease/pest resistance: Excellent resistance to Blackspot, Powdery Mildew, Downey Mildew, and Rust. Typically average resistance to normal pests of *Rosa* hybrid garden plants.

Temperature tolerance: Good heat tolerance, flowers can shows signs of fading earlier in high heat, with no other negative effects.

What is claimed is:

1. A new and distinct cultivar of shrub type *Rosa* hybrid plant named 'Noasplash' as herein illustrated and described.

* * * * *